(12) United States Patent
Nishi et al.

(10) Patent No.: US 7,189,543 B2
(45) Date of Patent: Mar. 13, 2007

(54) METHOD FOR PRODUCING CADAVERINE DICARBOXYLATE

(75) Inventors: Kiyohiko Nishi, Kawasaki (JP); Shuichi Endo, Kawasaki (JP); Yukiko Mori, Kawasaki (JP); Kazuhiko Totsuka, Kawasaki (JP); Yoshinori Hirao, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 410 days.

(21) Appl. No.: 10/851,318

(22) Filed: May 24, 2004

(65) Prior Publication Data
US 2005/0003497 A1 Jan. 6, 2005

(30) Foreign Application Priority Data
May 26, 2003 (JP) ............... 2003-147688

(51) Int. Cl.
C12P 13/00 (2006.01)
C12P 13/02 (2006.01)
C12N 1/20 (2006.01)
(52) U.S. Cl. .................. 435/129; 435/252.33; 435/488
(58) Field of Classification Search ................ 435/129, 435/252.33, 488
See application file for complete search history.

(56) References Cited

U.S. PATENT DOCUMENTS 5,989,875 A * 11/1999 Kojima et al. .............. 435/115

FOREIGN PATENT DOCUMENTS

| JP | SHO 49-126890 | 12/1974 | |
|----|---------------|---------|---|
| JP | 2002-223770 | 8/2002 | |
| JP | 2002-223771 | 8/2002 | |
| JP | 2003-292612 | 10/2003 | |
| JP | 2003292612 | * 10/2003 | |
| JP | 2003292614 | * 10/2003 | |
| JP | 2004208646 | * 7/2004 | |
| JP | 2005060447 | * 3/2005 | |

OTHER PUBLICATIONS

Maruo et al., "Enzyme Handbook (Koso Handbook)", Dec. 1, 1982, Kabushiki Kaisha Asakura Shoten, Shinjuku-ku, Tokyo, Japan, pp. 636-637.
Soda K. et al., "Crystalline Lysine Decarboxylase", Biochemical and Biophysical Research Communications, 1969, vol. 34, No. 1, pp. 34-39.
Sabo D. L. et al., "Purification and Physical Properties of Inducible *Escherichia coli* Lysine Decarboxylase", Biochemistry, 1974, vol. 13, No. 4, pp. 662-670.
Ramakrishna S. et al., "Decarboxylation of Homoarginine and Lysine by an Enzyme from *Lathyrus sativus* Eedlings", Phytochemistry, 1976, vol. 15, pp. 83-86.
Watson N. et al., "Identification of Elements Involved in Transcriptional Regulation of the *Escherichia coli* cad Operon by External pH", Journal of Bacteriology, 1992, vol. 174, No. 2, pp. 530-540.
Meng S. et al., "Nucleotide Sequence of the pi *Escherichia coli* cad Operon: a System for Neutralization of Low Extracellular pH", Journal of Bacteriology, 1992, vol. 174, No. 8, pp. 2659-2669.
Ise N. et al., "Introduction of New Polymer Chemistry" Mar. 25, 1995, Kabushiki Kaisha Kagaku Donin, Shimogyo-ku, Kyoto-shi, Japan, pp. 22-23.

* cited by examiner

*Primary Examiner*—Herbert J. Lilling
(74) *Attorney, Agent, or Firm*—Cermak & Kenealy, LLP; Shelly Guest Cermak

(57) ABSTRACT

Cadaverine dicarboxylate is produced by performing an enzymatic decarboxylation reaction of a lysine solution while adding a dicarboxylic acid containing 4 to 10 carbons to the lysine solution to maintain pH of the solution at a level sufficient for the enzymatic decarboxylation reaction to occur, for example, 4.0 to 8.0.

15 Claims, 1 Drawing Sheet

SEQUENCE LISTING

<160> NUMBER OF SEQ ID NOS: 4

<210> SEQ ID NO 1
<211> LENGTH: 25
<212> TYPE: DNA
<213> ORGANISM: artificial
<220> FEATURE:
<223> OTHER INFORMATION: primer

<400> SEQUENCE: 1
gtcgacactg cacatcggct ggcgg                                          25

<210> SEQ ID NO 2
<211> LENGTH: 25
<212> TYPE: DNA
<213> ORGANISM: artificial
<220> FEATURE:
<223> OTHER INFORMATION: primer

<400> SEQUENCE: 2
gttagcggca cgtacacctg cctgg                                          25

<210> SEQ ID NO 3
<211> LENGTH: 2148
<212> TYPE: DNA
<213> ORGANISM: Escherichia coli
<220> FEATURE:
<221> NAME/KEY: CDS
<222> LOCATION: (1)..(2148)

<400> SEQUENCE: 3

```
atg aac gtt att gca ata ttg aat cac atg ggg gtt tat ttt aaa gaa      48
Met Asn Val Ile Ala Ile Leu Asn His Met Gly Val Tyr Phe Lys Glu
 1               5                  10                  15 gaa ccc atc cgt gaa ctt cat cgc gcg ctt gaa cgt ctg aac ttc cag      96
Glu Pro Ile Arg Glu Leu His Arg Ala Leu Glu Arg Leu Asn Phe Gln
             20                  25                  30 att gtt tac ccg aac gac cgt gac gac tta tta aaa ctg atc gaa aac     144
Ile Val Tyr Pro Asn Asp Arg Asp Asp Leu Leu Lys Leu Ile Glu Asn
         35                  40                  45 aat gcg cgt ctg tgc ggc gtt att ttt gac tgg gat aaa tat aat ctc     192
Asn Ala Arg Leu Cys Gly Val Ile Phe Asp Trp Asp Lys Tyr Asn Leu
     50                  55                  60 gag ctg tgc gaa gaa att agc aaa atg aac gag aac ctg ccg ttg tac     240
Glu Leu Cys Glu Glu Ile Ser Lys Met Asn Glu Asn Leu Pro Leu Tyr
 65                  70                  75                  80 gcg ttc gct aat acg tat tcc act ctc gat gta agc ctg aat gac ctg     288
Ala Phe Ala Asn Thr Tyr Ser Thr Leu Asp Val Ser Leu Asn Asp Leu
                 85                  90                  95 cgt tta cag att agc ttc ttt gaa tat gcg ctg ggt gct gct gaa gat     336
Arg Leu Gln Ile Ser Phe Phe Glu Tyr Ala Leu Gly Ala Ala Glu Asp
            100                 105                 110 att gct aat aag atc aag cag acc act gac gaa tat atc aac act att     384
Ile Ala Asn Lys Ile Lys Gln Thr Thr Asp Glu Tyr Ile Asn Thr Ile
        115                 120                 125 ctg cct ccg ctg act aaa gca ctg ttt aaa tat gtt cgt gaa ggt aaa     432
Leu Pro Pro Leu Thr Lys Ala Leu Phe Lys Tyr Val Arg Glu Gly Lys
    130                 135                 140
```

-continued

| | |
|---|---|
| tat act ttc tgt act cct ggt cac atg ggc ggt act gca ttc cag aaa<br>Tyr Thr Phe Cys Thr Pro Gly His Met Gly Gly Thr Ala Phe Gln Lys<br>145     150     155     160 | 480 |
| agc ccg gta ggt agc ctg ttc tat gat ttc ttt ggt ccg aat acc atg<br>Ser Pro Val Gly Ser Leu Phe Tyr Asp Phe Phe Gly Pro Asn Thr Met<br>     165     170     175 | 528 |
| aaa tct gat att tcc att tca gta tct gaa ctg ggt tct ctg ctg gat<br>Lys Ser Asp Ile Ser Ile Ser Val Ser Glu Leu Gly Ser Leu Leu Asp<br>   180     185     190 | 576 |
| cac agt ggt cca cac aaa gaa gca gaa cag tat atc gct cgc gtc ttt<br>His Ser Gly Pro His Lys Glu Ala Glu Gln Tyr Ile Ala Arg Val Phe<br>     195     200     205 | 624 |
| aac gca gac cgc agc tac atg gtg acc aac ggt act tcc act gcg aac<br>Asn Ala Asp Arg Ser Tyr Met Val Thr Asn Gly Thr Ser Thr Ala Asn<br>210     215     220 | 672 |
| aaa att gtt ggt atg tac tct gct cca gca ggc agc acc att ctg att<br>Lys Ile Val Gly Met Tyr Ser Ala Pro Ala Gly Ser Thr Ile Leu Ile<br>225     230     235     240 | 720 |
| gac cgt aac tgc cac aaa tcg ctg acc cac ctg atg atg atg agc gat<br>Asp Arg Asn Cys His Lys Ser Leu Thr His Leu Met Met Met Ser Asp<br>     245     250     255 | 768 |
| gtt acg cca atc tat ttc cgc ccg acc cgt aac gct tac ggt att ctt<br>Val Thr Pro Ile Tyr Phe Arg Pro Thr Arg Asn Ala Tyr Gly Ile Leu<br>   260     265     270 | 816 |
| ggt ggt atc cca cag agt gaa ttc cag cac gct acc att gct aag cgc<br>Gly Gly Ile Pro Gln Ser Glu Phe Gln His Ala Thr Ile Ala Lys Arg<br>     275     280     285 | 864 |
| gtg aaa gaa aca cca aac gca acc tgg ccg gta cat gct gta att acc<br>Val Lys Glu Thr Pro Asn Ala Thr Trp Pro Val His Ala Val Ile Thr<br>290     295     300 | 912 |
| aac tct acc tat gat ggt ctg ctg tac aac acc gac ttc atc aag aaa<br>Asn Ser Thr Tyr Asp Gly Leu Leu Tyr Asn Thr Asp Phe Ile Lys Lys<br>305     310     315     320 | 960 |
| aca ctg gat gtg aaa tcc atc cac ttt gac tcc gcg tgg gtg cct tac<br>Thr Leu Asp Val Lys Ser Ile His Phe Asp Ser Ala Trp Val Pro Tyr<br>     325     330     335 | 1008 |
| acc aac ttc tca ccg att tac gaa ggt aaa tgc ggt atg agc ggt ggc<br>Thr Asn Phe Ser Pro Ile Tyr Glu Gly Lys Cys Gly Met Ser Gly Gly<br>   340     345     350 | 1056 |
| cgt gta gaa ggg aaa gtg att tac gaa acc cag tcc act cac aaa ctg<br>Arg Val Glu Gly Lys Val Ile Tyr Glu Thr Gln Ser Thr His Lys Leu<br>     355     360     365 | 1104 |
| ctg gcg gcg ttc tct cag gct tcc atg atc cac gtt aaa ggt gac gta<br>Leu Ala Ala Phe Ser Gln Ala Ser Met Ile His Val Lys Gly Asp Val<br>370     375     380 | 1152 |
| aac gaa gaa acc ttt aac gaa gcc tac atg atg cac acc acc act tct<br>Asn Glu Glu Thr Phe Asn Glu Ala Tyr Met Met His Thr Thr Thr Ser<br>385     390     395     400 | 1200 |
| ccg cac tac ggt atc gtg gcg tcc act gaa acc gct gcg gcg atg atg<br>Pro His Tyr Gly Ile Val Ala Ser Thr Glu Thr Ala Ala Ala Met Met<br>     405     410     415 | 1248 |
| aaa ggc aat gca ggt aag cgt ctg atc aac ggt tct att gaa cgt gcg<br>Lys Gly Asn Ala Gly Lys Arg Leu Ile Asn Gly Ser Ile Glu Arg Ala<br>   420     425     430 | 1296 |
| atc aaa ttc cgt aaa gag atc aaa cgt ctg aga acg gaa tct gat ggc<br>Ile Lys Phe Arg Lys Glu Ile Lys Arg Leu Arg Thr Glu Ser Asp Gly<br>     435     440     445 | 1344 |
| tgg ttc ttt gat gta tgg cag ccg gat cat atc gat acg act gaa tgc<br>Trp Phe Phe Asp Val Trp Gln Pro Asp His Ile Asp Thr Thr Glu Cys | 1392 |

```
                        450                    455                    460
tgg ccg ctg cgt tct gac agc acc tgg cac ggc ttc aaa aac atc gat           1440
Trp Pro Leu Arg Ser Asp Ser Thr Trp His Gly Phe Lys Asn Ile Asp
465                    470                    475                    480 aac gag cac atg tat ctt gac ccg atc aaa gtc acc ctg ctg act ccg           1488
Asn Glu His Met Tyr Leu Asp Pro Ile Lys Val Thr Leu Leu Thr Pro
                485                    490                    495 ggg atg gaa aaa gac ggc acc atg agc gac ttt ggt att ccg gcc agc           1536
Gly Met Glu Lys Asp Gly Thr Met Ser Asp Phe Gly Ile Pro Ala Ser
            500                    505                    510 atc gtg gcg aaa tac ctc gac gaa cat ggc atc gtt gtt gag aaa acc           1584
Ile Val Ala Lys Tyr Leu Asp Glu His Gly Ile Val Val Glu Lys Thr
        515                    520                    525 ggt ccg tat aac ctg ctg ttc ctg ttc agc atc ggt atc gat aag acc           1632
Gly Pro Tyr Asn Leu Leu Phe Leu Phe Ser Ile Gly Ile Asp Lys Thr
530                    535                    540 aaa gca ctg agc ctg ctg cgt gct ctg act gac ttt aaa cgt gcg ttc           1680
Lys Ala Leu Ser Leu Leu Arg Ala Leu Thr Asp Phe Lys Arg Ala Phe
545                    550                    555                    560 gac ctg aac ctg cgt gtg aaa aac atg ctg ccg tct ctg tat cgt gaa           1728
Asp Leu Asn Leu Arg Val Lys Asn Met Leu Pro Ser Leu Tyr Arg Glu
                565                    570                    575 gat cct gaa ttc tat gaa aac atg cgt att cag gaa ctg gct cag aat           1776
Asp Pro Glu Phe Tyr Glu Asn Met Arg Ile Gln Glu Leu Ala Gln Asn
            580                    585                    590 atc cac aaa ctg att gtt cac cac aat ctg ccg gat ctg atg tat cgc           1824
Ile His Lys Leu Ile Val His His Asn Leu Pro Asp Leu Met Tyr Arg
        595                    600                    605 gca ttt gaa gtg ctg ccg acg atg gta atg act ccg tat gct gca ttc           1872
Ala Phe Glu Val Leu Pro Thr Met Val Met Thr Pro Tyr Ala Ala Phe
610                    615                    620 cag aaa gag ctg cac ggt atg acc gaa gaa gtt tac ctc gac gaa atg           1920
Gln Lys Glu Leu His Gly Met Thr Glu Glu Val Tyr Leu Asp Glu Met
625                    630                    635                    640 gta ggt cgt att aac gcc aat atg atc ctt ccg tac ccg ccg gga gtt           1968
Val Gly Arg Ile Asn Ala Asn Met Ile Leu Pro Tyr Pro Pro Gly Val
                645                    650                    655 cct ctg gta atg ccg ggt gaa atg atc acc gaa gaa agc cgt ccg gtt           2016
Pro Leu Val Met Pro Gly Glu Met Ile Thr Glu Glu Ser Arg Pro Val
            660                    665                    670 ctg gag ttc ctg cag atg ctg tgt gaa atc ggc gct cac tat ccg ggc           2064
Leu Glu Phe Leu Gln Met Leu Cys Glu Ile Gly Ala His Tyr Pro Gly
        675                    680                    685 ttt gaa acc gat att cac ggt gca tac cgt cag gct gat ggc cgc tat           2112
Phe Glu Thr Asp Ile His Gly Ala Tyr Arg Gln Ala Asp Gly Arg Tyr
690                    695                    700 acc gtt aag gta ttg aaa gaa gaa agc aaa aaa taa                           2148
Thr Val Lys Val Leu Lys Glu Glu Ser Lys Lys
705                    710                    715

<210> SEQ ID NO 4
<211> LENGTH: 715
<212> TYPE: PRT
<213> ORGANISM: Escherichia coli

<400> SEQUENCE: 4

Met Asn Val Ile Ala Ile Leu Asn His Met Gly Val Tyr Phe Lys Glu
 1               5                  10                  15
```

-continued

```
Glu Pro Ile Arg Glu Leu His Arg Ala Leu Glu Arg Leu Asn Phe Gln
             20                  25                  30

Ile Val Tyr Pro Asn Asp Arg Asp Leu Leu Lys Leu Ile Glu Asn
         35                  40                  45

Asn Ala Arg Leu Cys Gly Val Ile Phe Asp Trp Asp Lys Tyr Asn Leu
     50                  55                  60

Glu Leu Cys Glu Glu Ile Ser Lys Met Asn Glu Asn Leu Pro Leu Tyr
 65                  70                  75                  80

Ala Phe Ala Asn Thr Tyr Ser Thr Leu Asp Val Ser Leu Asn Asp Leu
                 85                  90                  95

Arg Leu Gln Ile Ser Phe Phe Glu Tyr Ala Leu Gly Ala Ala Glu Asp
                100                 105                 110

Ile Ala Asn Lys Ile Lys Gln Thr Thr Asp Glu Tyr Ile Asn Thr Ile
            115                 120                 125

Leu Pro Pro Leu Thr Lys Ala Leu Phe Lys Tyr Val Arg Glu Gly Lys
        130                 135                 140

Tyr Thr Phe Cys Thr Pro Gly His Met Gly Gly Thr Ala Phe Gln Lys
145                 150                 155                 160

Ser Pro Val Gly Ser Leu Phe Tyr Asp Phe Phe Gly Pro Asn Thr Met
                165                 170                 175

Lys Ser Asp Ile Ser Ile Ser Val Ser Glu Leu Gly Ser Leu Leu Asp
            180                 185                 190

His Ser Gly Pro His Lys Glu Ala Glu Gln Tyr Ile Ala Arg Val Phe
        195                 200                 205

Asn Ala Asp Arg Ser Tyr Met Val Thr Asn Gly Thr Ser Thr Ala Asn
210                 215                 220

Lys Ile Val Gly Met Tyr Ser Ala Pro Ala Gly Ser Thr Ile Leu Ile
225                 230                 235                 240

Asp Arg Asn Cys His Lys Ser Leu Thr His Leu Met Met Met Ser Asp
                245                 250                 255

Val Thr Pro Ile Tyr Phe Arg Pro Thr Arg Asn Ala Tyr Gly Ile Leu
            260                 265                 270

Gly Gly Ile Pro Gln Ser Glu Phe Gln His Ala Thr Ile Ala Lys Arg
        275                 280                 285

Val Lys Glu Thr Pro Asn Ala Thr Trp Pro Val His Ala Val Ile Thr
    290                 295                 300

Asn Ser Thr Tyr Asp Gly Leu Leu Tyr Asn Thr Asp Phe Ile Lys Lys
305                 310                 315                 320

Thr Leu Asp Val Lys Ser Ile His Phe Asp Ser Ala Trp Val Pro Tyr
                325                 330                 335

Thr Asn Phe Ser Pro Ile Tyr Glu Gly Lys Cys Gly Met Ser Gly Gly
            340                 345                 350

Arg Val Glu Gly Lys Val Ile Tyr Glu Thr Gln Ser Thr His Lys Leu
        355                 360                 365

Leu Ala Ala Phe Ser Gln Ala Ser Met Ile His Val Lys Gly Asp Val
    370                 375                 380

Asn Glu Glu Thr Phe Asn Glu Ala Tyr Met Met His Thr Thr Thr Ser
385                 390                 395                 400

Pro His Tyr Gly Ile Val Ala Ser Thr Glu Thr Ala Ala Ala Met Met
                405                 410                 415
```

```
Lys Gly Asn Ala Gly Lys Arg Leu Ile Asn Gly Ser Ile Glu Arg Ala
            420                 425                 430

Ile Lys Phe Arg Lys Glu Ile Lys Arg Leu Arg Thr Glu Ser Asp Gly
            435                 440                 445

Trp Phe Phe Asp Val Trp Gln Pro Asp His Ile Asp Thr Thr Glu Cys
            450                 455                 460

Trp Pro Leu Arg Ser Asp Ser Thr Trp His Gly Phe Lys Asn Ile Asp
465                 470                 475                 480

Asn Glu His Met Tyr Leu Asp Pro Ile Lys Val Thr Leu Leu Thr Pro
                485                 490                 495

Gly Met Glu Lys Asp Gly Thr Met Ser Asp Phe Gly Ile Pro Ala Ser
            500                 505                 510

Ile Val Ala Lys Tyr Leu Asp Glu His Gly Ile Val Val Glu Lys Thr
            515                 520                 525

Gly Pro Tyr Asn Leu Leu Phe Leu Phe Ser Ile Gly Ile Asp Lys Thr
    530                 535                 540

Lys Ala Leu Ser Leu Leu Arg Ala Leu Thr Asp Phe Lys Arg Ala Phe
545                 550                 555                 560

Asp Leu Asn Leu Arg Val Lys Asn Met Leu Pro Ser Leu Tyr Arg Glu
                565                 570                 575

Asp Pro Glu Phe Tyr Glu Asn Met Arg Ile Gln Glu Leu Ala Gln Asn
            580                 585                 590

Ile His Lys Leu Ile Val His His Asn Leu Pro Asp Leu Met Tyr Arg
        595                 600                 605

Ala Phe Glu Val Leu Pro Thr Met Val Met Thr Pro Tyr Ala Ala Phe
    610                 615                 620

Gln Lys Glu Leu His Gly Met Thr Glu Glu Val Tyr Leu Asp Glu Met
625                 630                 635                 640

Val Gly Arg Ile Asn Ala Asn Met Ile Leu Pro Tyr Pro Pro Gly Val
            645                 650                 655

Pro Leu Val Met Pro Gly Glu Met Ile Thr Glu Glu Ser Arg Pro Val
            660                 665                 670

Leu Glu Phe Leu Gln Met Leu Cys Glu Ile Gly Ala His Tyr Pro Gly
            675                 680                 685

Phe Glu Thr Asp Ile His Gly Ala Tyr Arg Gln Ala Asp Gly Arg Tyr
    690                 695                 700

Thr Val Lys Val Leu Lys Glu Glu Ser Lys Lys
705                 710                 715
```

METHOD FOR PRODUCING CADAVERINE DICARBOXYLATE

BACKGROUND OF THE INVENTION

1. Field of the Invention

The present invention relates to a method for producing cadaverine dicarboxylate. Cadaverine dicarboxylate can be used as a raw material for producing nylon.

2. Description of the Related Art

Naphtha, a fossil material, is a major raw material in the production of plastics. Disposal of plastics which are not recycled has recently become a environmental concern due to the release of carbon dioxide when disposed of by burning, etc. Accordingly, with the goal of preventing global warming and encouraging a recycling society, it is strongly desirable to replace raw materials for producing plastics with those derived from biomass.

Polylactic acid is known as a plastic produced using biomass as a raw material. A method for producing polylactic acid includes first extracting starch or sugar from a plant, then producing lactic acid by fermentation using the extracted starch or sugar as a carbon source, and then chemically polymerizing the resulting lactic acid. Polylactic acid is expected to be used in various industrial products, including container packages, garments, and others. However, since polylactic acid has a melting point of about 190° C., it is not suitable for high temperature uses.

Plastics which have high heat resistance include nylon, particularly polyamide. An example of a widely-used nylon is nylon-66, which is produced by polymerizing hexamethylenediamine, which is a diamine containing 6 carbons, and adipic acid, which is a dicarboxylic acid containing 6 carbons, at a molar ratio of 1:1. Since nylon-66 has a melting point of 250° C. or higher, it is a plastic material which is able to withstand high temperature conditions.

The aforementioned hexamethylenediamine is produced using benzene, propylene, or butadiene and can be obtained from the raw material naphtha. However, production methods from biomass are unknown. On the other hand, pentamethylenediamine containing 5 carbons, also known as cadaverine, is known to be produced from lysine, an amino acid, using lysine decarboxylase (hereinafter "LDC") (Enzyme Handbook, 1st ed., p. 636, Asakura Shoten). Therefore, if nylon is produced using a pentamethylenediamine containing 5 carbons as a raw material instead of hexamethylenediamine containing 6 carbons, it is then possible to provide a plastic material produced using a raw material derived from biomass and usable under high temperature conditions.

LDC is known to exist in bacteria such as *Bacterium cadaveris* (Soda K. et al., Biochem. Biophys. Res. Com., Vol. 34, pp. 34–39, 1969) and *Escherichia coli* (*E. coli*) (Sabo D. L. et al., Biochemistry, Vol. 13, pp. 662–670, 1974) and plants such as *Lathyrus sativus* (Ramakrishna S. et al., Phytochemistry, Vol. 15, pp. 83–86, 1976). LDC can be extracted from these organisms and used for the production of cadaverine. Furthermore, the sequence of the LDC gene (cadA) of *E. coli* is known (Watson N. et al., Journal of Bacteriology, Vol. 174, pp. 530–540, 1992; Meng S. Y. et al. Journal of Bacteriology, Vol. 174, pp. 2659–2669, 1992). Furthermore, a method of producing cadaverine by culturing a host in which enzymatic activity of LDC or the lysine-cadaverine antiporter is amplified using such an LDC gene or the like has been suggested (Japanese Patent Laid-open (Kokai) No. 2002-223770), and a method of producing cadaverine by allowing LDC derived from a recombinant cell in which the intracellular activity of LDC is amplified to act on lysine has also been suggested (Japanese Patent Laid-open No. 2002-223771).

However, if LDC is allowed to act on lysine, carbon dioxide is released by the decarboxylation reaction of LDC, and hence the pH is raised by the production of cadaverine during the reaction. Therefore, to prevent the rise of pH and maintain the optimal pH for the enzymatic reaction, it is necessary to perform the reaction in a buffer of a high concentration, or successively add an acid to the reaction system to neutralize the alkalinity (Japanese Patent Laid-open (Kokai) Nos. 2002-223770 and 2002-223771). In general, inorganic acids such as hydrochloric acid, sulfuric acid and phosphoric acid or organic acids such as acetic acid are often used for neutralization of pH during an enzymatic reaction. When alkalinity is neutralized with these acids, the cadaverine which is obtained from the reaction mixture is in the form of a salt such as cadaverine hydrochloride, cadaverine sulfate, cadaverine phosphate and cadaverine acetate.

Known methods for producing nylons include condensation polymerization of a dicarboxylic acid dihalide and a diamine in the presence of a base. Alternatively, a method of heating a salt or a lower condensate, which has formed from a dicarboxylic acid and a diamine under melting conditions, to polycondense is known (Ise, N. et al., Shinkobunshika-gakujoron, p. 22, Kagakudojin, 1995). When cadaverine is obtained by the enzymatic reaction and then polymerized with a dicarboxylic acid by either method, free cadaverine must be re-prepared from a salt of cadaverine. Therefore, the process becomes complicated and is no longer economical.

Furthermore, a method for producing lysine by fermentation is known, and includes culturing a bacterium in a medium containing adipic acid, succinic acid, fumaric acid or a salt thereof as a main component, and maintained at pH 7.5 to 8.2 with ammonium hydroxide (Japanese Patent Laid-open No. 49-126890). In this method, the bacterium is sub-cultured to allow proliferation thereof and maintain dynamic equilibrium of cells, and then the cells are cultured with changing a part of the medium conditions or culture conditions to perform fermentation with a shifted equilibrium of substance metabolism and thereby accumulate lysine in the medium at a high concentration.

SUMMARY OF THE INVENTION

An object of the present invention is to provide a method for economically producing cadaverine as a diamine to be used as a raw material for production of nylon in a form easily and most efficiently used in the polymerization.

It is a further object of the present invention to provide a method for producing a cadaverine dicarboxylate comprising subjecting a lysine solution to an enzymatic decarboxylation reaction and maintaining the pH of said solution at a level sufficient for said reaction to occur by adding dicarboxylic acid to said solution.

It is a further object of the present invention to provide the method as described above, wherein pH of the solution is maintained at about 4.0 to 8.0.

It is a further object of the present invention to provide the method as described above, wherein the dicarboxylic acid contains 4 to 10 carbons.

It is a further object of the present invention to provide the method as described above, wherein the dicarboxylic acid is adipic acid.

It is a further object of the present invention to provide the method as described above, wherein the enzymatic decarboxylation reaction is performed using lysine decarboxylase, a cell producing lysine decarboxylase or a processed product of the cell producing lysine decarboxylase.

It is a further object of the present invention to provide the method as described above, wherein the cell is modified to have increased lysine decarboxylase activity.

It is a further object of the present invention to provide the method as described above, wherein the cell is recombinant.

It is still a further object of the present invention to provide the method as described above wherein the cell is modified to have increased copy number of a gene encoding lysine decarboxylase.

It is a still further object of the present invention to provide the method as described above, wherein the cell is modified by modifying an expression regulatory sequence of a gene encoding lysine decarboxylase.

It is a still further object of the present invention to provide the method as described above, wherein the expression of the gene encoding lysine decarboxylase is enhanced.

It is a still further object of the present invention to provide the method as described above, wherein the cell is an *Escherichia coli* cell.

It is a still further object of the present invention to provide the method as described above, wherein the gene encoding lysine decarboxylase is a cadA gene.

It is a still further object of the present invention to provide a method of producing nylon comprising subjecting a lysine solution to an enzymatic decarboxylation reaction, maintaining the pH of said solution at a level sufficient for said reaction to occur by adding dicarboxylic acid to the solution to produce cadaverine dicarboxylate, and polycondensing said cadaverine dicarboxylate.

According to the present invention, cadaverine dicarboxylate can be simply and efficiently produced. The cadaverine dicarboxylate obtained by the present invention can be used in a polymerization reaction for producing nylon.

DESCRIPTION OF THE PREFERRED EMBODIMENTS

Figure 1:
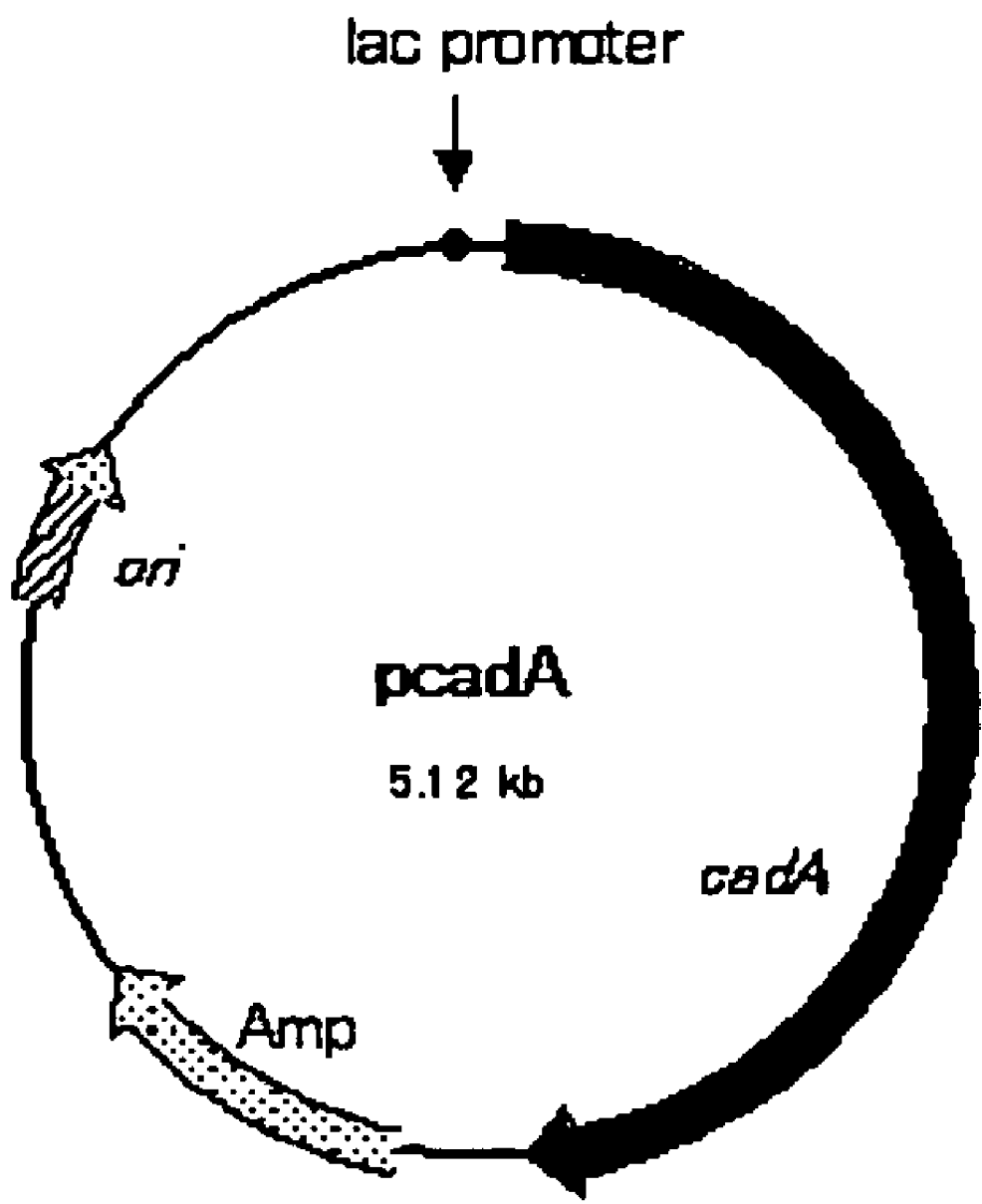
FIG. 1 shows a structure of a plasmid pcadA containing the cadA gene of *E. coli*.

The inventors of the present invention assiduously studied in order to achieve the foregoing object. The present invention describes a decarboxylation reaction of lysine can produce cadaverine as dicarboxylate using free lysine as a raw material in the enzymatic decarboxylation reaction of lysine, adjusting pH of a lysine solution to a level optimal for the enzymatic reaction with addition of a dicarboxylic acid, allowing LDC to act on the solution and further performing the decarboxylation reaction while adding the aforementioned dicarboxylic acid to neutralize pH increasing during the enzymatic decarboxylation reaction, and thus accomplished the present invention.

Hereafter, the present invention will be explained in detail.

In the method of the present invention, cadaverine dicarboxylate is produced by performing an enzymatic decarboxylation reaction of lysine in a lysine solution while adding a dicarboxylic acid to maintain pH of the solution at a level sufficient for the enzymatic decarboxylation reaction to occur.

Usually, the raw material lysine is preferably a free base (lysine base). However, it may be a salt of lysine with a dicarboxylic acid. Although the lysine may be either L-lysine or D-lysine, so long as cadaverine is produced by an enzymatic decarboxylation reaction, L-lysine is usually preferred. Furthermore, the lysine used in the method of the present invention may be purified lysine, or may be in the form of a fermentation broth containing lysine, so long as cadaverine produced by the enzymatic decarboxylation reaction can form a salt with a dicarboxylic acid.

Water is preferable as the solvent used for the preparation of the lysine solution. In the present invention, since the pH of the reaction mixture is adjusted with a dicarboxylic acid, there is no need to use any other pH modifier or buffer. However, a buffer may be used as the aforementioned solvent. Examples of such a buffer include a sodium acetate buffer and so forth. However, for the purpose of forming of a salt of cadaverine dicarboxylate, it is preferable either not to use a buffer, or to use a buffer having a low concentration.

When free lysine is used in the present invention, a dicarboxylic acid is added to the lysine solution to adjust the pH of the solution to a level sufficient for the enzymatic decarboxylation reaction to occur. Specifically, the pH is usually between about 4.0 and 8.0, preferably between about 5.0 and 7.0, and more preferably between about 5.5 and 6.5. When a lysine dicarboxylate is used, the dicarboxylic acid does not need to be added at the time of preparation of the reaction mixture. Hereinafter, the adjustment of the pH of the reaction mixture to a level sufficient for the enzymatic decarboxylation reaction to occur described above may be called "neutralization".

The aforementioned dicarboxylic acid is not particularly limited so long as it does not inhibit the enzymatic decarboxylation reaction of lysine, and can produce nylon by a condensation polymerization reaction with cadaverine. Examples thereof include a dicarboxylic acid containing 4 to 10 carbons, preferably a dicarboxylic acid consisting of a straight molecule having carboxyl groups at both ends. Specific examples thereof include succinic acid, glutaric acid, adipic acid, pimelic acid, suberic acid, azelaic acid, sebacic acid, and so forth. The dicarboxylic acid is preferably a free acid.

The enzymatic decarboxylation reaction of lysine can be performed by adding LDC to a lysine solution which has been neutralized as described above. The aforementioned LDC is not particularly limited so long as it can act on lysine to produce cadaverine. Cells producing LDC may be used to obtain LDC, including microorganisms, plant cells or animal cells. Purified LDC may also be used. A mixture of various sources of LDC may also be used. Furthermore, the cells may be used as they are, or a cell-processed product containing LDC may be used. Examples of a cell-processed product include a cell-disrupted suspension and a fraction thereof. When the enzymatic reaction is performed using microbial cells, plant cells or animal cells, it is known that if the cells are treated with an organic solvent, a detergent or the like, permeability of the substance from the outside of the cells may be improved and reactivity may be increased. Therefore, treating LDC-producing cells with an organic solvent, a detergent or the like may also result in an increase of reactivity of the enzymatic decarboxylation reaction of lysine. Examples of the detergent used for treating the cells include Triton X-100, Tween 20, sodium cholate, CHAPS or the like, and examples of the organic solvent include acetone, xylene, toluene or the like. More specifically, in case of using Triton X-100, it is preferable that Triton X-100 is added to the cell suspension at a concentration of between 0.01% to 1.0% (w/v), and the cells are treated at 0° C. to 37° C. for 2 min to 1 hour.

Examples of the aforementioned microorganisms include bacteria belonging to the genus *Escherichia*, such as *E. coli*, coryneform bacteria such as *Brevibacterium lactofermentum*, bacteria belonging to the genus *Bacillus* such as *Bacillus subtilis*, bacteria belonging to the genus *Serratia* such as *Serratia marcescens*, eukaryotic cells such as *Saccharomyces cerevisiae* and so forth. Among these, a bacterium, in particular, *E. coli* is preferred.

The aforementioned microorganism may be a wild-type or a mutant strain, so long as it is able to produce LDC. Furthermore, the microorganism may be a recombinant strain modified so that its LDC activity is increased. The aforementioned plant and animal cells may be recombinant cells which have been modified so that the LDC activity is increased. The recombinant cells will be described later.

After LDC is added to a lysine solution, the reaction starts and the carbon dioxide which is released is discharged from the reaction mixture, and the pH is raised as the reaction progresses. A dicarboxylic acid is added to the reaction mixture to maintain the pH of the reaction mixture in the aforementioned range. The dicarboxylic acid used is usually the same dicarboxylic acid that is used to neutralize the raw material lysine. The dicarboxylic acid may be continuously or periodically added, so long as pH is maintained in the aforementioned range. Although the reaction conditions are not particularly limited so long as LDC can act on lysine to produce cadaverine, the reaction is usually performed at a temperature of 20 to 60° C., preferably at 30 to 40° C.

The entire amount of raw material lysine or lysine dicarboxylate may be added to the reaction mixture at the start of the reaction, or may be added gradually during the LDC reaction.

If the enzymatic reaction is performed in batches, the dicarboxylic acid can be easily added. Furthermore, the reaction can also be performed by employing a moving bed column chromatography using a carrier immobilized with LDC, cells producing LDC or a processed product thereof. In this case, lysine and the dicarboxylic acid can be injected into an appropriate site on a column so that the reaction progresses while maintaining the pH of the reaction system within a predetermined range.

As described above, by neutralizing pH raised along with the production of cadaverine by the enzymatic decarboxylation reaction of lysine with use of a dicarboxylic acid as required, the enzymatic reaction favorably progresses. Cadaverine produced as described above accumulates in the reaction mixture as a dicarboxylic acid salt.

The cadaverine dicarboxylate obtained by the LDC reaction can be isolated or purified from the reaction mixture using combinations of known methods. For example, the reaction mixture can be sterilized using an autoclave or the like, and a supernatant is collected by centrifugation, discolored using activated carbon or the like and concentrated as required. The cadaverine dicarboxylate may be in the form of a solution as is, or a crystal depending on the use. Crystals of the cadaverine dicarboxylate can be formed by precipitating the cadaverine dicarboxylate while cooling the concentrated reaction mixture, for example. The crystals obtained as described above are preferred as a raw material for producing nylon, because the crystals contain cadaverine and the dicarboxylic acid in equimolar amounts.

Nylon is produced by polycondensing the cadaverine dicarboxylate produced according to the present invention. An embodiment of the present invention includes a method for producing nylon comprising the steps of producing a cadaverine dicarboxylate via an enzymatic decarboxylation reaction of lysine while maintaining the pH at a level sufficient for enzymatic decarboxylation by adding a dicarboxylic acid to a lysine solution, and producing nylon by polycondensing the cadaverine dicarboxylate obtained in the aforementioned step.

An example of a method for modifying a microorganism so that its LDC activity is increased will be explained below. The LDC activity in other cells can also be similarly increased by suitably modifying the following method.

The LDC activity is increased, for example, by enhancing expression of the gene encoding LDC (LDC gene). The expression of the LDC gene can be enhanced by increasing the copy number of the LDC gene. For example, an LDC gene fragment is ligated to a vector which is able to function in a microorganism, preferably a multi-copy type vector, to prepare a recombinant DNA which is then used to transform a suitable host.

Increasing the copy number of the LDC gene can also be accomplished by introducing multiple copies of the gene on chromosomal DNA of the microorganism. Multiple copies of the LDC gene may be introduced into the chromosomal DNA of a microorganism by homologous recombination. This is done by targeting a sequence present on chromosomal DNA in multiple copy number. A repetitive DNA or inverted repeat present at the end of a transposable element can be used as the sequence present on a chromosomal DNA in a multiple copy number. Alternatively, as disclosed in Japanese Patent Laid-open No. 2-109985, multiple copies of the desired gene can be introduced into a chromosomal DNA by incorporating them into a transposon and transferring it.

Besides the gene amplification method discussed above, the LDC activity can also be increased by replacing an expression regulatory sequence, such as a promoter of the LDC gene, on a chromosomal DNA or a plasmid with a stronger one. For example, lac promoter, trp promoter, trc promoter and so forth are known as strong promoters. Furthermore, as disclosed in International Patent Publication WO00/18935, a promoter can also be modified to be a stronger one by introducing substitution of several nucleotides into the promoter region of the gene. The aforementioned substitution or modification of the promoter enhances expression of the LDC gene, and thus the LDC activity is increased. Modification of an expression regulatory sequence can be combined with increasing the copy number of the gene.

Substitution of the expression regulatory sequence can be performed, for example, in the same manner as in gene substitution using a temperature sensitive plasmid. Examples of a vector having a temperature-sensitive replication origin of *E. coli* include, for example, plasmid pMAN997 described in International Patent Publication WO99/03988 and the like. Furthermore, substitution of an expression regulatory sequence can also be performed by a method using Red recombinase of λ phage (Datsenko, K. A., PNAS, 97(12), 6640–6645, 2000).

The LDC gene is not particularly limited so long as the encoded LDC can be effectively used for the decarboxylation reaction of lysine. Examples thereof include LDC genes of bacteria such as *Bacterium cadaveris* and *E. coli* and plants such as *Lathyrus sativus* as well as the LDC gene of the microorganism described in Japanese Patent Laid-open No. 2002-223770.

When *E. coli* is used as a host microorganism, an LDC gene derived from *E. coli* is preferred. As the LDC gene from *E. coli*, the cadA gene and the ldc gene (U.S. Pat. No. 5,827,698) are known. Among these, the cadA gene is preferred. The sequence of the cadA gene of *E. coli* is known (Watson N. et al., Journal of Bacteriology, Vol. 174, 530–540, 1992; Meng S. Y. et al. Journal of Bacteriology, Vol. 174, 2659–2669, 1992: GenBank accession number M76411). The cadA gene can be isolated from an *E. coli* chromosomal DNA by PCR using primers prepared based on that sequence. Examples of such primers include primers having the nucleotide sequences of SEQ ID NOS: 1 and 2. The nucleotide sequence of the cadct gene as stated above and the amino acid sequence encoded by the cada gene are shown in SEQ ID NOS: 3 and 4, respectively.

To prepare a recombinant DNA by ligating the LDC gene and a vector, the vector can be digested with restriction enzymes suitable for the ends of the LDC gene, and the aforementioned gene and the vector can be ligated using a ligase such as T4 DNA ligase. Examples of the vector for *E. coli* include pUC18, pUC19, pSTV29, pHSG299, pHSG399, pHSG398, RSF1010, pBR322, pACYC184, pMW219 and so forth.

The LDC gene may be a wild-type gene or a mutant gene. For example, the cadA gene may encode LDC including substitution, deletion, insertion or addition of one or several amino acid residues at one or more sites so long as the LDC activity is not diminished. Although the number of "several" amino acids referred to herein varies depending on positions of amino acid residues in the three-dimensional structure of the protein and types of the amino acid residues. However, it is specifically 2 to 50, preferably 2 to 30, more preferably 2 to 10.

Therefore, changes to LDC such as those described above are are typically conservative changes so as to maintain LDC activity. Substitution changes include those in which at least one residue in the amino acid sequence has been removed and a different residue inserted in its place. Examples of amino acids which may be substituted for an original amino acid in a LDC protein and which are regarded as conservative subsitutions include: Ala substituted with ser or thr; arg substituted with gln, his, or lys; asn substituted with, gln, lys, or his; asp substituted with asn, glu, or gln; cys substituted with ser or ala; gln substituted with asn, glu, lys, his, asp, or arg; glu substituted with asn, gln, lys, or asp; gly substituted with pro; his substituted with asn, lys, gln, arg, tyr; ile substituted with leu, met, val, phe; leu substituted with ile, met, val, phe; lys substituted with asn, glu, gln, his, arg; met substituted with ile, leu, val, phe; phe substituted with trp, tyr, met, ile, or leu; ser substituted with thr, ala; thr substituted with ser or ala; trp substituted with phe, tyr; tyr substituted with his, phe, or trp; and val substituted with met, ile, leu.

A DNA encoding a protein substantially identical to the aforementioned LDC can be obtained by modifying the nucleotide sequence of the cadA gene. For example, site-directed mutagenesis can be employed so that substitution, deletion, insertion, addition or inversion of an amino acid residue or residues occur at a specific site. Furthermore, a DNA modified as described above can also be obtained by conventionally-known mutation treatments. Examples of such mutation treatments include treating DNA before the mutation treatment in vitro with hydroxylamine or the like, treating a microorganism, for example, an *Escherichia* bacterium, containing DNA before the mutation treatment with ultraviolet ray irradiation or a mutagenesis agent used in a usual mutation treatment such as N-methyl-N'-nitro-N-nitrosoguanidine (NTG) or EMS, and so forth.

A DNA encoding a protein substantially identical to LDC can be obtained by expressing such a DNA including any of the aforementioned mutations in a suitable cell and examining the activity of the expression product. Furthermore, for example, a DNA which is hybridizable with a probe having the sequence of the coding region of the cadA gene (GenBank accession number M76411) or a part of this sequence under stringent conditions and encodes a protein having the same activity as LDC at a comparable level can be obtained from a DNA encoding LDC having a mutation or a cell containing the DNA. The "stringent conditions" include a condition under which a so-called specific hybrid is formed, and a non-specific hybrid is not formed. It is difficult to clearly express this condition using any numerical value. However, the stringent conditions include, for example, a condition whereby DNAs having high homology, for example, DNAs having a homology of 70% or more, preferably 80% or more, more preferably 90%, most preferably 95% or more hybridize with each other, whereas DNAs having a homology lower than the above do not hybridize with each other. Alternatively, stringent conditions are exemplified by conditions whereby DNAs hybridize with each other at a salt concentration corresponding to ordinary conditions of washing in Southern hybridization, i.e., 1×SSC, 0.1% SDS, preferably 0.1×SSC, 0.1% SDS, at 60° C.

A partial sequence of the cadA gene can also be used as a probe. Probes can be generated by PCR using oligonucleotides prepared based on the known nucleotide sequence of the cadA gene as primers, and a DNA fragment containing the cadA gene as a template. When a DNA fragment of about 300 bp is used as the probe, the washing conditions for hybridization can be, for example, 2×SSC, 0.1% SDS at 50° C.

Examples of a DNA encoding a protein substantially identical to LDC include a DNA encoding a protein having a homology of preferably 70% or more, more preferably 80% or more, even more preferably 90% or more, most preferably 95% or more with the amino acid sequence encoded by the known cadA gene and having the LDC activity.

In order to introduce a recombinant DNA into a microorganism, any known transformation methods that have hitherto been reported can be employed. For instance, the methods include a method of treating recipient cells with calcium chloride so as to increase the permeability of the cells for DNA, which has been reported for *Escherichia coli* K-12 (Mandel, M. and Higa, A., J. Mol. Biol., 53, 159 (1970)), and a method of preparing competent cells from cells which are at the growth phase followed by introducing the DNA thereinto, which has been reported for *Bacillus subtilis* (Duncan, C. H., Wilson, G. A. and Young, F. E., Gene, 1, 153 (1977)). Furthermore, the methods of transformation include a method of making DNA-recipient cells into protoplasts or spheroplasts, which can easily take up a recombinant DNA, followed by introducing the recombinant DNA into the DNA-acceptor cells, which is known for *Bacillus subtilis,* actinomycetes and yeasts (Chang, S. and Choen, S. N., Molec. Gen. Genet., 168, 111 (1979); Bibb, M. J., Ward, J. M. and Hopwood, O. A., Nature, 274, 398 (1978); Hinnen, A., Hicks, J. B. and Fink, G. R., Proc. Natl. Sci., USA, 75, 1929 (1978)). The transformation of microorganism can also be performed by the electric pulse method (Japanese Patent Laid-open No. 2-207791).

Culture for obtaining a microorganism or cell which produces LDC can be performed according to a method suitable for the production of LDC depending on the microorganism or cell used.

For example, the medium may be a usual medium containing a carbon source, nitrogen source, inorganic ions and other organic components as required. As the carbon source, saccharides such as glucose, lactose, galactose, fructose, arabinose, maltose, xylose, trehalose, ribose and hydrolysate of starch, alcohols such as glycerol, mannitol and sorbitol and organic acids such as gluconic acid, fumaric acid, citric acid and succinic acid can be used. As the nitrogen source, inorganic ammonium salts such as ammonium sulfate, ammonium chloride and ammonium phosphate, organic nitrogen such as soybean hydrolysate, ammonia gas, aqueous ammonia and so forth can be used. As for organic trace nutrients, it is preferable to add required substances, for example, vitamins such as vitamin $B_1$, nucleic acids such as adenine and RNA, yeast extract and so forth in suitable amounts. In addition to these substances, small amounts of calcium phosphate, magnesium sulfate, iron ion, manganese ion and so forth can be added, as required.

In the case of *Escherichia coli*, for example, the culture is preferably performed under aerobic conditions for about 16 to 72 hours. The culture temperature is controlled to be between 30 to 45° C., and pH is controlled to be between 5 and 8 during the culture. Inorganic or organic, acidic or alkaline substances as well as ammonia gas and so forth can be used to adjust pH.

When expression of the LDC gene is controlled by an inducible promoter, an inducer can be added to the medium.

After the culture, the cells can be collected from the culture broth using a centrifuge or membrane. The cells may be used as is. However, when a processed product thereof containing LDC is to be used, the cells can be disrupted by ultrasonication, treatment with a French press or treatment with enzymes to extract the enzyme and prepare a cell-free extract. When LDC is further purified from the extract, it can be purified by salting out with ammonium sulfate or various chromatography techniques in a conventional manner.

EXAMPLES

The present invention will be explained more specifically with reference to the following non-limiting examples.

Example 1

Construction of a LDC-amplified Strain of *Escherichia coli*

PCR primers having the nucleotide sequences of SEQ ID NOS: 1 and 2 were designed based on the nucleotide sequence of the LDC gene (cadA) of *E. coli* (Watson N. et al., Journal of Bacteriology, Vol. 174, 530–540, 1992; Meng S. Y. and Bennet G. N., Journal of Bacteriology, Vol. 174, 2659–2669, 1992) and used for PCR with the chromosome of *E. coli* W3110 (ATCC 39936) as a template to amplify a DNA fragment containing the cada gene.

To prepare the pcadA plasmid, the amplified DNA fragment was digested with KpnI and SphI, and the resulting fragment (2468 bp) was inserted into the KpnI-SphI digestion site of pUC18 (Takara Shuzo) (FIG. 1). The *E. coli* JM109 strain (Takara Shuzo) was transformed with the pcadA plasmid. A transformant was selected using ampicillin resistance as a marker, and designated *E. coli* JM109/pcadA.

Example 2

Production of Cadaverine Adipate from Lysine Adipate Using cadA-amplified Strain (1) Culture of cadA-amplified Strain

*E. coli* JM109/pcadA was precultured in the LB medium, and then 50 ml of the culture broth was inoculated into 500 ml of the LB medium of two-fold concentration (2% of trypton, 1% of yeast extract, 1% of NaCl) contained in a 1-L jar fermenter (ABLE Co., Ltd.). The cells were cultured with aeration and stirring under the following conditions: aeration rate of 250 ml/min, 35° C. and 700 rpm. Following a 15 hour culture, the whole culture broth was inoculated into 22 L of LB medium of two-fold concentration contained in a 50-L jar fermenter, and the culture was continued under the following conditions: aeration rate of 11 L/min, 35° C., an internal pressure in the jar of 50 kPa and 250 rpm. Following the 4 hour culture, 3 g of IPTG (isopropyl-β-D-thiogalactopyranoside) was dissolved in 50 ml of water and added to the culture through a filter. Then, the culture was continued for 22 hours.

(2) Isolation of Cells

The cells were collected from the culture broth using a tubular separator at 17,000 rpm with a feeding rate of 550 ml/min. The collected cells were scraped from a sheet in a cylinder and suspended in 1 L of physiological saline. The wet weight of the collected cells was 147 g.

(3) Production of Cadaverine Adipate

To prepare a lysine adipate substrate solution, adipic acid was added to a 50% (w/v) lysine base solution (Daiichi fine chemical Co., Ltd) so that the solution had a pH of 6.0. To prepare a reaction mixture, the substrate solution was then added to water to a final concentration of 50 g/L relative to the lysine concentration, and pyridoxal phosphate was added to the mlxture to a concentration of 0.1 mM. The *E. coli* JM109/pcadA cell suspension (wet weight of cells: 147 g) was added to the reaction mixture to initiate a reaction. The reaction was performed in 22 L of the reaction mixture charged in a 50-L jar fermenter. The reaction was performed under the following conditions: 37° C., aeration of 1/10 vvm, 250 rpm and an internal pressure of 5 kPa. The reaction mixture was adjusted to pH 6.0 by adding adipic acid slurry (250 g/kg $H_2O$).

The substrate solution corresponding to 1 kg of lysine was added after 2 hours and 3 hours of the reaction, and the reaction was allowed to continue. After 6 hours, almost 100% of lysine was converted into cadaverine. Lysine and cadaverine were measured by the post-column OPA method using HPLC (Vale S. R. and Gloria M. B., Journal Of AOAC International, Vol. 80, 1006–1012, 1997). The measurement results were as follows.

| | |
|---|---|
| Cadaverine concentration | 69 g/L (0.68 M) |
| Adipic acid concentration | 105 g/L (0.72 M) |
| Remaining lysine concentration | <1 g/l |
| Amount of obtained cadaverine | 2.2 kg (21 mol) |
| Amount of charged lysine | 3.1 kg (21 mol) |
| Conversion yield | 100% (mol/mol) |

As described above, a cadaverine adipate solution containing cadaverine and adipic acid in equimolar amounts was obtained.

Example 3

Acquisition of Cadaverine Adipate Crystals (1) Removal of Cells from Cadaverine Adipate Solution The cadaverine adipate solution obtained in Example 2 was sterilized in an autoclave at 120° C. for 10 minutes and centrifuged to collect a supernatant.

(2) Decoloration and Concentration

The obtained supernatant was added to 20% activated carbon based on the cadaverine weight and decolored with stirring at 20° C. for 1 hour. The activated carbon was removed using filter paper, and the obtained filtrate was concentrated 4- to 5-fold under reduced pressure (55 to 60° C., 110 to 150 mmHg). The solid content of the concentrate was 70 to 77%.

(3) Crystallization of Cadaverine Adipate and Separation of Crystals

The aforementioned concentrate was cooled from 60° C. to 10° C. at 4° C./hour to precipitate crystals. The crystallization rate was 40 to 45%. The precipitated crystals were separated and collected using a centrifuge and air-dried in a desiccator for several days. When the obtained crystals were analyzed by X-ray crystallography (AFC-5S produced by Rigaku Corporation, analytical program: TEXAN), they were found to consist of cadaverine adipate dihydrate, and the purity was 99% or higher. These crystals contain cadaverine and adipic acid in equimolar amounts and can be used for a polymerization reaction of nylon as is.

Example 4

Production of Cadaverine Succinate from Lysine Succinate Using CadA-amplified Strain

*E. coli* JM109/pcadA was inoculated into 50 ml of the LB medium and 100 mg/L of ampicillin contained in a 500-mL Sakaguchi flask. The cells were precultured at 28° C. for 8 hours. 12 ml of the culture broth was inoculated into 500 ml of the LB medium of two-fold concentration contained in a 1-L jar fermentor (ABLE Co., Ltd.). The cells were cultured with aeration and stirring under the following conditions: aeration rate of 250 ml/min, 35° C. and 700 rpm. Following the 3.5 hour culture, IPTG (isopropyl-β-D-thiogalactopyranoside) was added to a final concentration of 0.67 mM to the culture broth. Then, the culture was continued for 12.5 hours. The culture broth was centrifuged at 8,000 rpm for 10 min, and the supernatant was removed to collect the cells. The wet weight of the collected cells was 10.3 g per 1 liter of culture broth. The cells were reserved at −80° C. in a frozen state. The cells were thawed on ice, and suspended in a deionized water to obtain an enzyme solution prior to use.

To prepare a lysine succinate substrate, succinic acid was added to a 50% (w/v) lysine base solution (Daiichi fine chemical) so that the solution had a pH of 6.0. To prepare a reaction mixture, water was added to the substrate solution to a final concentration of 100 g/L relative to the lysine concentration, and pyridoxal phosphate was added to the mixture to a concentration of 0.1 mM. The *E. coli* JM109/pcadA cell suspension (wet weight of cells: 0.309 g) was added to the reaction mixture to initiate a reaction. The reaction was performed with 0.3 L of the reaction mixture in a 1-L jar fermentor. The reaction was performed under the following conditions: 37° C., aeration of 1/10 vvm, 200 rpm. The reaction mixture was adjusted to pH 6.0 by adding an equimolar amount of crystalline succinic acid (24.23 g) to lysine. Then, the reaction was allowed to continue for 3 hours without pH control. The pH of the reaction mixture indicated 7.2 at the end of the reaction.

Lysine and cadaverine were measured by the post-column OPA method using HPLC. The results were as follows. Decarboxylation progressed successfully, and a cadaverine succinate solution containing cadaverine and succinic acid in equimolar amounts was obtained.

| | |
|---|---|
| Cadaverine concentration | 66.8 g/L (0.654 M) |
| Remaining lysine concentration | 0.17 g/L |
| Succinic acid concentration | 78.3 g/L (0.663 M) |
| Amount of obtained cadaverine | 20.4 g (201 mmol) |
| Amount of charged lysine | 30 g (204 mmol) |
| Conversion yield | 98.6% |

Example 5

Production of Cadaverine Sebacate from Lysine Sebacate Using cadA-amplified Strain The *E. coli* JM109/pcadA was cultured in a 1-L jar fermentor (ABLE Co., Ltd.) and the cells were collected in the same manner as in Example 4.

To prepare a lysine sebacate substrate solution, sebacic acid was added to a 50% (w/v) lysine base solution (Daiichi fine chemical) so that the solution had a pH of 6.6. To prepare the reaction mixture, water was added to the substrate solution to a final concentration of 100 g/L relative to the lysine concentration, and pyridoxal phosphate was added to the mixture to a concentration of 0.1 mM. The *E. coli* JM109/pcadA cell suspension (wet weight of cells: 0.309 g) was added to the reaction mixture to initiate a reaction. The reaction was performed with 0.3 L of the reaction mixture in a 1-L jar fermentor. The reaction was performed under the following conditions: 37° C., aeration of 1/10 vvm, 200 rpm. The reaction mixture was adjusted to pH 6.6 by adding an equimolar amount of crystalline sebacic acid (41.51 g) to lysine. Then, the reaction was continued for 3 hours without pH control. The pH of the reaction mixture indicated 7.1 at the end of the reaction.

Lysine and cadaverine were measured by the post-column OPA method using HPLC. The results were as follows. Decarboxylation progressed successfully, and a cadaverine sebacate solution containing cadaverine and sebacic acid in equimolar amounts was obtained.

| | |
|---|---|
| Cadaverine concentration | 63.9 g/L (0.625 M) |
| Remaining lysine concentration | 0.17 g/L |
| Sebacic acid concentration | 128.9 g/L (0.637 M) |
| Amount of obtained cadaverine | 20.4 g (200 mmol) |
| Amount of charged lysine | 30 g (204 mmol) |
| Conversion yield | 98.1% |

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety, including the foreign priority document, JP2003-147688.

What is claimed is:

1. A method for producing a cadaverine dicarboxylate comprising
   A) subjecting a lysine solution to an enzymatic decarboxylation reaction;
   B) maintaining the pH of said solution at a level sufficient for said reaction to occur by adding dicarboxylic acid to said solution.

2. The method of claim 1, wherein the pH is about 4.0 to 8.0.

3. The method of claim 1, wherein said dicarboxylic acid contains 4 to 10 carbons.

4. The method of claim 3, wherein said dicarboxylic acid is adipic acid.

5. The method of claim 1, wherein the enzymatic decarboxylation reaction is performed using lysine decarboxylase, a cell producing lysine decarboxylase, or a processed product of a cell producing lysine decarboxylase.

6. The method of claim 5, wherein said cell is modified to have increased lysine decarboxylase activity.

7. The method of claim 6, wherein said cell is recombinant.

8. The method of claim 6, wherein said cell is modified to have an increased copy number of a gene encoding lysine decarboxylase.

9. The method of claim 6, wherein said cell is modified by modifying an expression regulatory sequence of a gene encoding lysine decarboxylase.

10. The method of claim 9, wherein the expression of said gene encoding lysine decarboxylase is enhanced.

11. The method of claim 5, wherein said cell is an *Escherichia coli* cell.

12. The method of claim 8, wherein said gene encoding said lysine decarboxylase is a cadA gene.

13. A method for producing a cadaverine dicarboxylate comprising:
- A) subjecting a lysine solution to an enzymatic decarboxylation reaction;
- B) maintaining the pH of said solution at between about 4.0 and 8.0 by adding dicarboxylic acid to said solution.

14. A method for producing a cadaverine dicarboxylate comprising:
- A) subjecting a lysine solution to an enzymatic decarboxylation reaction by adding lysine decarboxylase;
- B) maintaining the pH of said solution at between about 4.0 and 8.0 by adding dicarboxylic acid to said solution.

15. A method of producing nylon comprising:
- A) subjecting a lysine solution to an enzymatic decarboxylation reaction;
- B) maintaining the pH of said solution at a level sufficient for said reaction to occur by adding dicarboxylic acid to said solution to produce cadaverine dicarboxylate; and
- C) polycondensing said cadaverine dicarboxylate.

* * * * *